(12) United States Patent
Golz-Berner et al.

(10) Patent No.: US 7,892,523 B2
(45) Date of Patent: Feb. 22, 2011

(54) COSMETIC PROCESS FOR THE TREATMENT OF THE SKIN WITH SUN-PROTECTION PRODUCTS AND SUN-PROTECTION PRODUCTS COMBINATION

(75) Inventors: Karin Golz-Berner, Monaco (MC); Leonhard Zastrow, Monaco (MC)

(73) Assignee: Coty B.V., Haarlem (NL)

( * ) Notice: Subject to any disclaimer, the term of this patent is extended or adjusted under 35 U.S.C. 154(b) by 1066 days.

(21) Appl. No.: 11/568,092

(22) PCT Filed: Apr. 14, 2005

(86) PCT No.: PCT/EP2005/004150

§ 371 (c)(1), (2), (4) Date: Oct. 19, 2006

(87) PCT Pub. No.: WO2005/102260

PCT Pub. Date: Nov. 3, 2005

(65) Prior Publication Data

US 2009/0117060 A1    May 7, 2009

(30) Foreign Application Priority Data

Apr. 20, 2004    (DE) .................. 10 2004 020 060

(51) Int. Cl.
  *A61K 8/00*    (2006.01)
  *A61K 8/18*    (2006.01)
  *A61K 9/00*    (2006.01)
  *A61K 8/02*    (2006.01)
  *A61Q 17/04*    (2006.01)

(52) U.S. Cl. .................. 424/59; 424/400; 424/401

(58) Field of Classification Search .................. 424/59, 424/401
See application file for complete search history.

(56) References Cited

U.S. PATENT DOCUMENTS 6,399,046 B1    6/2002    Schoenrock et al.
6,426,080 B1 *  7/2002    Golz-Berner et al. ........ 424/401
6,861,077 B1 *  3/2005    Cannell et al. .............. 424/725
2002/0006383 A1 * 1/2002    Anderson et al. ............. 424/40
2002/0012714 A1 * 1/2002    Olson ......................... 424/766
2003/0125584 A1 * 7/2003    Sonnenberg et al. ......... 568/327
2003/0147825 A1 * 8/2003    Chiarelli et al. .......... 424/70.11
2003/0185770 A1 * 10/2003   Birrenbach .................. 424/59
2003/0223982 A1 * 12/2003   Schlotmann et al. ...... 424/94.61
2004/0052749 A1 * 3/2004    Golz-Berner et al. .... 424/70.13
2004/0059110 A1 * 3/2004    Nakano et al. ................ 544/60
2004/0202684 A1 * 10/2004   Djerassi ..................... 424/401
2006/0029555 A1 * 2/2006    Bernstein .................... 424/59
2007/0036735 A1 * 2/2007    Kitasaki ...................... 424/63

FOREIGN PATENT DOCUMENTS

| EP | 0 010 483 A | 4/1980 |
| FR | 2 674 126 A | 9/1992 |
| FR | 2 831 444 A | 5/2003 |
| WO | 94 17781 A | 8/1994 |
| WO | 01 26617 A | 4/2001 |

* cited by examiner

*Primary Examiner*—Sreeni Padmanabhan
*Assistant Examiner*—Luke E Karpinski
(74) *Attorney, Agent, or Firm*—Norris McLaughlin & Marcus, PA

(57) ABSTRACT

The invention relates to a cosmetic method, whereby skin is treated with various sun products, and to a sun product combination. The inventive method is characterized by applying, prior to intensive exposure of the skin to UV radiation, a pre-sun product, then a sun product and finally repeatedly applying an after-sun product. The pre-sun product comprises a radical interceptor, the combination caffeine/complex amino acid salt, the combination photolyase/UV endonuclease and an algae extract of *Corallina officinalis*. The sun product comprises a UV filter combination of UVA and UVB filters having at least 3% by weight of UVA filter. The after-sun product comprises components similar to those used for the pre-sun product, the content of the radical interceptor and the enzyme photolyase being by 50 to 90% by weight lower, the content of the enzyme UV endonuclease being by 50 to 90% by weight higher, and the algae extract being replaced by a cooling plant extract.

15 Claims, 1 Drawing Sheet

Figure 1:
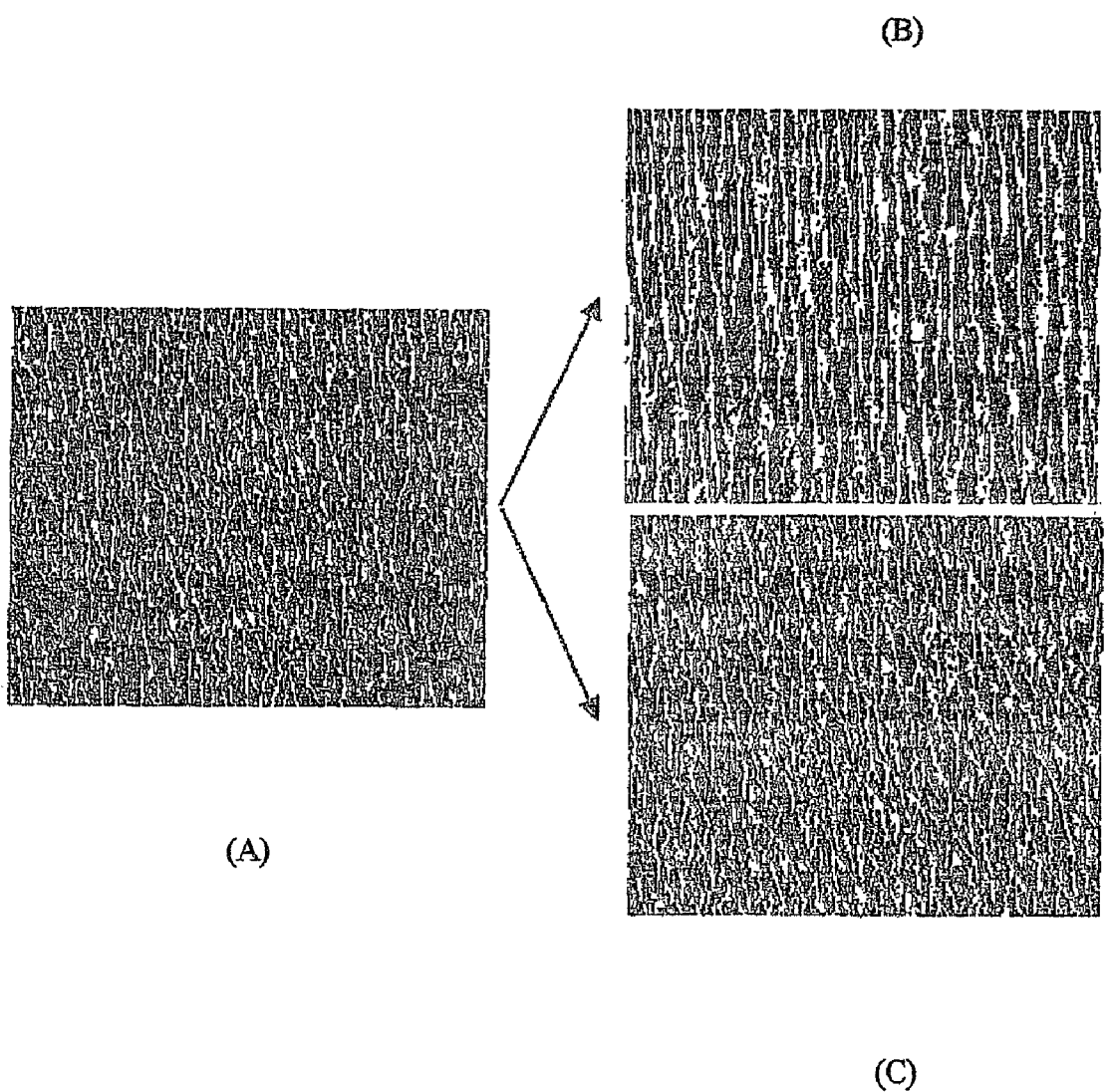

COSMETIC PROCESS FOR THE TREATMENT OF THE SKIN WITH SUN-PROTECTION PRODUCTS AND SUN-PROTECTION PRODUCTS COMBINATION

The invention relates to a cosmetic method in which the skin is treated with various sun products as well as to a sun product combination.

A large number of cosmetic sunscreens is known, which contain sun filters in different compositions and quite often are intended to provide sufficient UVB protection only. In addition, products with a self-tanning effect are known, as well as products which are applied to the skin once the exposure to sunlight has finished, e.g. after-sun sprays. EP-A-1380279 discloses a formulation with a skin care effect and specific UV filter combinations.

The object of the invention is to provide a novel sun product combination which achieves an improved sun protection effect, an improved tan and, at the same time, has a skin care effect, as well as a cosmetic method for treating the skin with the aforesaid sun product combination.

According to the invention, said method for treating the skin with sun products consists in that (a) prior to intensive exposure to UV radiation, a pre-sun product is applied to the skin one to several time(s) a day for between 2 and 7 days, which product comprises as essential ingredients a radical scavenger, a combination of caffeine and complex amino acid salts, a combination of the enzyme photolyase enclosed in liposomes and UV endonuclease, and an algae extract from *Corallina officinalis*, (b) in case of intensive exposure to UV radiation, a sun product is applied to the skin, comprising a UV filter combination of UVA filters and UVB filters containing at least 3% by weight of UVA filters, relative to the total weight of the sun product, and (c) after intensive exposure to UV radiation, an after-sun product is applied to the skin at least once or one to several time(s) for between 1 and 7 days, which product comprises essentially the same ingredients as the pre-sun product, the content of the radical scavenger and the enzyme photolyase being 50-90% by weight lower, the content of the enzyme UV endonuclease being 50-90% by weight higher, in both cases relative to the total weight of said products, and the algae extract being replaced with a cooling plant extract or a plant extract mixture.

It is preferred that the pre-sun product be applied two to three times a day for between 5 and 7 days and the after-sun product be applied two to three times a day for between 3 and 6 days.

In a preferred embodiment of the invention, a sun product is applied which contains at least 3.5% by weight of organic UVA filters, of which 0.3 to 0.7% by weight is a photostable organic UVA filter and 2.8 to 3.2% by weight is a photoinstable organic UVA filter, relative to the total weight of the sun product.

Preferably, a sun product with a sun protection factor (SPF) ranging between SPF 8 and SPF 30 is applied.

"Intensive exposure to sunlight" means an amount of radiation which is achieved either by exposure of the skin to direct natural sunlight on a light, sandy beach for more than 30 minutes or by exposure to artificial radiation generated by a sun simulator (XBO xenon lamp, 450 W/20 FR) with $E_{UVA}$=8.4 mW/cm$^2$ and $E_{UVB}$=0.18 mW/cm$^2$ for more than 20 minutes, the aforesaid exposures being repeated for at least 3 to 6 days.

Further, the invention relates to a sun product combination consisting of a pre-sun product, a sun product and an after-sun product, wherein the pre-sun product comprises as essential ingredients a radical scavenger, a combination of caffeine and complex amino acid salts, a combination of the enzyme photolyase enclosed in liposomes and UV endonuclease, and an algae extract from *Corallina officinalis*, the sun product comprises a UV filter combination of UVA filters and UVB filters containing at least 3% by weight of UVA filters, relative to the total weight of the sun product, and the after-sun product comprises essentially the same ingredients as the pre-sun product, the content of the radical scavenger and the enzyme photolyase being 50-90% by weight lower, the content of the enzyme UV endonuclease being 50-90% by weight higher, in both cases relative to the total weight of said products, and the algae extract being replaced with a cooling plant extract or plant extract mixture.

In another embodiment of the invention, the inventive sun product is provided as a set consisting of a pre-sun product, a sun product and an after-sun product whose weight ratio is 1:0.5-2:0.8-1.

It is preferred that the amounts contained be as follows: radical scavenger 0.1-2% by weight; combination of caffeine/complex amino acid salts 0.01-3.0% by weight with a ratio of 1:10-300, the caffeine content being max. 0.5%; photolyase and UV endonuclease together in the range of 0.1-1.5% by weight; algae extract 0.2-2.5% by weight; and plant extract 0.1-2.5% by weight, all percentages being relative to the total weight of the sun product concerned.

Water- and/or oil-soluble UVA and UVB filters can be added. Advantageous broad spectrum filters which can be used and which are effective in the UVA range and in the UVB range alike include Benzophenone-3 and Benzophenone-4.

Advantageous UVB filters include derivatives of 4-aminobenzoic acid such as 4-(dimethylamino)-benzoic acid-(2-ethylhexyl)ester; esters of cinnamic acid such as 4-methoxy cinnamic acid (2-ethylhexyl)ester, derivatives of 3-benzylidene camphor such as 3-benzylidene camphor or sulphonic acid derivatives thereof, Octyl Methoxycinnamate, Isoamyl p-Methoxycinnamate, Ethylhexyl Methoxycinnamate, Octyl Salicylate, 4-Methylbenzylidene Camphor, Homosalate and Octyl Dimethyl PABA, sulphonic acid derivatives of benzophenone or salts such as the Na salt or K salt of 2-phenylbenzimidazol-5-sulphonic acid or salicylic acid derivatives such as Ethylhexyl Salicylate.

Preferred UVA filters are Butyl Methoxydibenzoylmethane, 1-phenyl-4-(4'-isopropylphenyl)propane-1,3-dione, Menthyl Anthranilate and Bis-Ethylhexyloxyphenol/Methoxyphenyl Triazine.

UVA/UVB filters can also be used, e.g. UV-Pearls (Merck, Germany).

Other UVA filters also include inorganic pigments based on metal oxides, such as $TiO_2$, $SiO_2$, ZnO, $Fe_2O_3$, $ZrO_2$, MnO, $Al_2O_3$, which can also be used as mixtures.

Particularly preferred inorganic filters are agglomerated substrates of $TiO_2$ and/or ZnO, which substrates contain spherical and porous $SiO_2$ particles, wherein said $SiO_2$ particles have a particle size ranging between 0.05 µm and 1.5 µm and, in addition to said $SiO_2$ particles, other inorganic, particle-shaped substances with a spherical structure are present, said spherical $SiO_2$ particles and said other inorganic substances forming defined agglomerates whose particle size ranges between 0.06 µm and 5 µm (according to WO99/06012).

UVB rays, whose wavelengths range between 290 and 320 nm, only penetrate into the epidermis up to a depth of approx. 50 µm, whereas UVA rays penetrate into the lower dermis layer, i.e. up to a depth of approx. 3 mm. Therefore, the production of free radicals in the skin is mainly due to the UVA range of the solar spectrum. In known sunscreens, however, the UVA range is often not sufficiently covered by filters, so that free radicals can form without limitation and, as a consequence, corresponding tissue damage is noticed late. In the present invention, the content of organic UVA filters is therefore at least 3%, preferably 3.5%, and in case of higher SPFs, in particular, is increased even further by physical filters.

A preferred combination of organic UVA filters is e.g. Butyl Methoxydibenzoylmethane (Parsol® 1789) making up 3.0% by weight and Bis-Ethylhexyloxyphenol/Methoxyphenyl Triazine (Tinosorb® S) making up 0.5% by weight.

Surprisingly, it has been found that a photostable UVA filter, such as e.g. Bis-Ethylhexyloxyphenol/Methoxyphenyl Triazine, can have a stabilizing effect on a photoinstable filter, such as Butyl Methoxydibenzoylmethane or Tinosorb® M, so that, overall, a relatively stable UVA filter mixture is obtained. This finding also led to the aforesaid specific, preferred ratio of UVA filters to one another.

In addition, 0.3-0.7% by weight of UV-Pearls® (Merck, Germany), which consist of water, Ethylhexyl Methoxycinnamate, Silica, PVP, Ethanol, Sodium Citrate, Chlorphenesin, Centrimonium Chloride, can be added as a broad spectrum filter.

Complex amino acid salts are preferably mixtures of histidine-HCl, arginine-HCl, ornithine-HCl, tyrosine and glutathione, preferably mixed with a polysaccharide such as sorbitol; an example of such a mixture is Phototan® LS2261E produced by Laboratoires Serobiologiques, Pulnoy, FR.

Moreover, it is necessary that radical scavengers be added which are able to eliminate free radicals, in case these are produced. Said scavengers make up 0.1-2% by weight, relative to the product's total weight.

A known and particularly effective radical scavenger for the inventive preparation is an active agent with a high radical protection factor, comprising a product obtained by extracting the bark of Quebracho blanco and subsequent enzymatic hydrolysis, which product contains at least 90% by weight proanthocyanidine oligomers and max. 10% by weight gallic acid, in microcapsules, and a silkworm extract obtained by extraction, which extract contains the peptide cecropine, amino acids and a vitamin mixture, and a non-ionic, cationic or anionic hydrogel or hydrogel mixture, and one or several phospholipid(s), and water (RPF complex). Reference is made to WO99/66881, e.g. active complex according to Example 1 or 2, or to WO01/26617, e.g. active complex according to Example 1. The aforesaid complex, which herein is referred to as RPF complex, can be supplemented by adding the product obtained by the decomposition of yeasts mentioned before as another active agent and an orange extract obtained by extracting fruits with propylene glycol.

Advantageously, the inventive cosmetic sun product contains 0.1-1% by weight of the aforesaid RPF complex with a high radical protection factor, the RPF of the pre-sun product ranging between 60 and 2,000×10$^{14}$ radicals/mg, thus being higher than that of usual cosmetic formulations with specified radical scavengers, which reach values of approx. 10 to 40. It is advantageous that the content of the radical scavenger in the sun product and in the after-sun product be 80-90% below the content in the pre-sun product.

The radical protection factor (RPF) defines the activity of an antioxidant with regard to the binding of free radicals in the form of a test substance. This test substance consists of a highly reactive, semi-stable radical, such as DMPO (5,5'-dimethyl-1-pyrrolin-N-oxide) or PBN (phenyl-tert-butyl nitrone), which reacts with all known antioxidants. The RPF is determined by measuring the signal amplitude of the test radical by means of electron spin resonance (ESR/EPR) before and after mixing said radical with an antioxidant and calculating the RPF from the measuring results. A number of standard antioxidants have known RPFs, e.g. for all-trans-retinol it is 827, for all-trans-retinol acetate it is 196; for DL-α-tocopherol it is 41,200 and for α-tocopherol acetate it is 48, in each case ×10$^{14}$ radicals/mg.

The measuring method is described in detail by Herrling, Groth, Fuchs and Zastrow in Conference Materials "Modern Challenges to the Cosmetic Formulation", 5-7 May 1997, Düsseldorf, pp. 150-155, Verlag f. chem. Ind., 1997. Based on the known concentration of the test radical or the number of free radicals of the same (radicals per ml), a signal amplitude $S_1$ is measured by means of an ESR spectrometer. Said test radical is dissolved in an aqueous/alcoholic solution, as is the antioxidant. Then, the signal amplitude $S_2$ of the antioxidant is measured. The normalized difference between the two signal amplitudes is the reduction factor RF.

$$RF = (S_1 - S_2)/S_1$$

The result of the reduction of the test radical RC×RF is normalized relative to the product input PI (mg/ml). The radical protection factor is calculated according to the equation:

$$RPF = \frac{RC[\text{radicals/ml}] \times RF}{PI[\text{mg/ml}]}$$

The result is RPF=N×10$^{14}$ [radicals per mg], wherein N is a positive, real number, which, in general, is stated without "×10$^{14}$" (cf. WO99/66881).

The combination of caffeine/complex amino acid salts surprisingly increases microcirculation. In addition, it enhances the tan of the skin brought about by the UV radiation. "Enhance" means that the tan lasts particularly long, i.e. for up to 8 days. The complex amino acid salt consists of sorbitol, arginine-HCl, ornithine-HCl, tyrosine and $SiO_2$. A preferred combination is caffeine/Phototan® LS2261E.

Preferably, the combination of caffeine/complex amino acid salts makes up 0.01-3.0% by weight of the inventive sun product, the ratio of caffeine to complex amino acid salts being 1:10-300. However, the caffeine content is max. 0.5% by weight.

In the inventive sun product combination, the sun product can additionally contain an active agent having a wrinkle-smoothing effect, such as e.g. Colhibin and hydrolyzed rice proteins, which protect collagen from the detrimental effects of collagenases and whose collagenase inhibitor activity is not less than 20 collagenase inhibitor units.

The algae extract from *Corallina officinalis* used in the inventive pre-sun product enhances the radical scavenging effect of the preferred RPF complex due to an enzymatic catalytic activity and a great variety of trace elements, such as iron, copper, iodine, cobalt, manganese. A preferred product is Oligophycocorail (produced by Semca, Pontrieux, France). Preferably, the extract is used in propylene glycol.

Further, the inventive preparation contains cosmetic auxiliaries and carriers as they are commonly used in such preparations, e.g. water, preservatives, colourants, pigments having a colouring effect, thickeners, fragrances, alcohols, polyols, esters, electrolytes, gel-forming agents, polar and non-polar oils, polymers, copolymers, emulsifiers, waxes, stabilizers.

Other active agents can also be contained. These include e.g. moisturizers, emollients, antioxidants, vitamins, enzymes, plant-based active agents, polymers, anti-inflammatory natural active agents, asymmetric lamellar aggregates loaded with oxygen according to WO94/00109; products obtained by the gentle ultrasonic decomposition of yeasts or vegetable matter according to WO94/13783, kaolin and kaolin which has been modified with $SiO_2$ according to WO94/17588.

Antioxidants used as additional active agents include vitamins, such as vitamin C and derivatives thereof, e.g. ascorbyl acetate, ascorbyl phosphate and ascorbyl palmitate; vitamin A and derivatives thereof; folic acid and derivatives thereof; vitamin E and derivatives thereof, such as tocopheryl acetate; flavons or flavonoids; amino acids, such as histidine, glycine, tyrosine, tryptophan and derivatives thereof; carotenoids and carotenes, such as α-carotene, β-carotene; uric acid and derivatives thereof; α-hydroxy acids, such as citric acid, lactic acid, malic acid; stilbene and derivatives thereof; and various plant extracts.

A plankton extract is incorporated as an active agent via liposomes, e.g. an extract which is obtained from cyanobacteria of the genus *Anacystes nidulans* and contains an effective amount of the enzyme photolyase. Said enzyme contributes to that cyclobutane pyrimidine dimers which have formed due to UV radiation are split up again in the presence of daylight, thus achieving a repair effect for the skin.

It is particularly advantageous that the aforesaid plankton extract be encapsulated in special liposomes made up of three kinds of phospholipids: phosphatidylethanolamine, phosphatidylcholine/oleic acid and cholesteryl hemisuccinate. Such liposomes have a great penetration force in keratinocytes and release their contents suddenly when the pH value reduces, e.g. from pH 6 to pH 4. A preferred product containing said plankton extract is Photosomes® produced by Barnet Products Corp., NJ/USA.

A *Micrococcus* lysate containing the enzyme UV endonuclease, which has long-lasting skin repair effects, is also incorporated via liposomes. Said liposomes can be embodied in the same advantageous way as those described for the plankton extract. A preferred product is Ultrasomes® produced by Barnet Products Corp., NJ/USA.

Photolyase and UV endonuclease in the form of the commercial products mentioned above make up 0.1-1.5% by weight. It is advantageous that the content of the enzyme photolyase in the after-sun product be 75-90% below the photolyase content in the pre-sun product.

Further, it is advantageous that a revitalizing active complex be added to the inventive sun product or after-sun product or both. Said complex consists of 1 to 9% by weight creatine or a creatine derivative, 0.1 to 40% by weight of water-soluble glycogen, 1 to 10% by weight of a phospholipid, 0.1 to 5% by weight of a cosmetically acceptable gel, water making up the remainder up to 100% by weight (according to WO02/060394). This active complex reduces the production of LDH (LDH=lactodeshydrogenase, a stress enzyme which is produced by the cells when they are exposed to UVB radiation). In addition, treatment of the cells with said complex increases the cells' oxygen consumption as a sign of cell vitality and the cells are repaired, thus making the cells appear younger and look better. The aforedescribed effect is a synergistic effect since the sum of the individual effects of glycogen and creatine is clearly exceeded, both in the anti-UV test (up to +153%) and in the oxygen consumption test (up to +174%). Said complex can be added in an amount of 0.5-5% by weight, relative to the preparation's weight.

Overall, the inventive sun product considerably reduces the risk of free radical formation and, at the same time, combines these very good UV protection properties with skin care properties provided by the pre-sun and after-sun products.

While usual products containing UVA and UVB filters do not have a ratio of said filters to one another above 1:3, the present invention increases said ratio to approx. 1:1.8-2.2. In addition, the inventive combination of photostable and photoinstable UVA filters with the ratios specified above is particularly effective as regards protection of the skin from damage caused by UVA rays.

Moreover, pretreatment of the skin with the pre-sun product combining the aforesaid ingredients brings about a particular care effect, which provides an excellent base for subsequent exposure to sunlight if said product is applied within the proposed time frame.

Even if the skin is exposed intensively to sunlight for a longer time, it looks very well, is substantially without DNA damage and negative wrinkle formation and shows a healthy tan for a long time.

Surprisingly, the relatively small amount of the plant extract, especially a water melon extract, added to the after-sun product as a moisturizer has a particularly long-lasting effect when combined with the other ingredients of the product and with the prior treatment described above. In comparative tests, it was found that the moisturizing effect to be expected was exceeded 1.5-1.8 times due to interaction with the other required ingredients of the preparation.

The extract from water melon (*Citrullus vulgaris*) is a water/glycerine extract containing at least 2% of fruit components. Said extract makes up 0.1-2.0% by weight, particularly 0.1-0.5% by weight, relative to the total weight of the after-sun product.

A rose flower extract and a jasmine flower extract (in both cases with water/glycerine) or mixtures of such plant extracts are also advantageous and serve the same purpose. A particularly advantageous extract mixture consists of water melon, rose and jasmine and, in total, makes up 1.5-2.5% by weight.

Overall, the sun protection combination improves the supply of the skin with protective and regenerating agents, thus considerably increasing the skin's resistance to UV radiation, ensuring a healthy appearance of the skin and largely preventing damage.

The inventive method and the sun product combination also have particular importance for artificial tanning in solariums in the dark season. Both contribute to a considerable improvement of the combination of UV protection/skin care, particularly when applied as described above. In this context, the term "exposure to sunlight" or "exposure to UV radiation" as used herein also refers to the radiation of lamps in solariums, etc., where sunlight is simulated.

The oils used for the invention can be common cosmetic oils, such as a mineral oil, hydrogenated polyisobutene, synthetic squalane or squalane made from natural products, cosmetic esters or ethers which can be branched or unbranched, saturated or unsaturated; vegetable oils; or mixtures of two or more thereof.

Particularly suitable oils are e.g. silicone oils and vegetable oils, such as calendula oil, jojoba oil, avocado oil, macadamia nut oil, castor oil, cocoa butter, coconut oil, maize oil, etc.

The inventive preparation can also be formulated with gel-forming agents. Suitable gel-forming agents include Carbomere, xanthan gum, carrageenan, acacia gum, guar gum, agar-agar, alginates and tyloses, carboxymethyl cellulose, hydroxyethyl cellulose, quaternized cellulose, quaternized guar, certain polyacrylates, polyvinyl alcohol, polyvinylpyrrolidone, montmorillonite. Carbomere is particularly preferred.

In addition, pigments, pigment mixtures or powders having a pigment-like effect can be added, which include those with a pearlescent effect. These can include e.g. iron oxides, natural aluminosilicates such as ochre, titanium dioxide, mica, kaolin, clays containing manganese, calcium carbonate, talcum, mica-titanium oxide, mica-titanium oxide-iron oxide, bismuth oxychloride, nylon globules, ceramic globules, expanded and non-expanded synthetic polymer powders, powdery natural organic compounds such as ground solid algae, ground parts of plants, encapsulated and non-encapsulated cereal starches and mica-titanium oxide-organic colourant.

Polyols can also be contained in the inventive sun product. Polyols are e.g. propylene glycol, dipropylene glycol, ethylene glycol, isoprene glycol, glycerine, butylene glycol, sorbitol and mixtures thereof. The polyol makes up between 2 and 10% by weight, preferably between approx. 2% and approx. 7% by weight, relative to the product's total weight.

The invention will now be explained in detail by means of examples. All quantities are in percent by weight unless indicated otherwise. In the attached drawing, FIG. 1 shows electron microscopic images of wrinkle formation in the skin.

EXAMPLE 1

Cream I, SPF*² 8

Phase A

Water q.s. ad 100, Propylene Glycol 2.0, Xanthan Gum 0.25, Acrylates Crosspolymer 0.5, Caffeine 0.5.

*² SPF=Sun Protection Factor (e.g. Cole, C. in Photoderm. Photoimmun. Photomed. 17:2-10, 2001).

Phase B

Isoamyl p-Methoxycinnamate 6.0, Ethylhexyl Salicylate 4.0, Butyl Methoxydibenzoylmethane 3.0, Bis-Ethylhexyloxyphenol/Methoxyphenyl Triazine 0.5, Ethylhexyl Methoxycinnamate 5.0, Dicaprylyl Carbonate 5.0, UV-Pearls® 0.5.

Phase C

Ethanol 3.0, RPF Complex* 0.5, Preservative 1.5, Photosomes® 0.6, Ultrasomes® 0.1, Vitamin E and *Micrococcus* Lysate in Liposomes 0.1, Hydrolyzed Rice Protein 0.5, Soy Protein 0.5, Phototan® 0.5, Perfume 0.8.

* Extract from the bark of Quebracho blanco, hydrolyzed enzymatically and encapsulated in microcapsules, silkworm extract with phospholipids and water in gel, WO99/66881, active complex according to Example 1.

Phases A and B are prepared separately, heated up to 75° C. and stirred into one another. The mixture is homogenized for a longer time, i.e. approx. 1-20 minutes, at 2,800-3,200 rpm and then cooled down to 40° C. Phase C is stirred in and the mixture is stirred for a few more minutes.

EXAMPLE 2

Cream II, SPF 8

Phase A

Water q.s. ad 100, Propylene Glycol 2.0, Xanthan Gum 0.25, Acrylates Crosspolymer 0.5, Caffeine 0.5.

Phase B $TiO_2$ 5.0, ZnO 2.0, Ethylhexyl Salicylate 4.0, Bis-Ethylhexyloxyphenol/Methoxyphenyl Triazine 0.5, Methylene Bis-Benzo-triazyl/Tetramethylbutylphenol/Decyl Glycosine/PPG/Xanthan Gum/Water (Tinosorb M®) 2.0, Ethylhexyl Methoxycinnamate 5.0, Dicaprylyl Carbonate 5.0, UV-Pearls® 0.5.

Phase C

Ethanol 3.0, RPF Complex* 0.5, Preservative 1.0, Photosomes® 0.6, Ultrasomes® 0.1, Vitamin E and *Micrococcus* Lysate in Liposomes 0.1, Hydrolyzed Rice Protein 0.5, Soy Protein 0.5, Phototan® 0.5, Perfume 0.8.

Processing was done as in Example 1. * see Example 1

* Extract from the bark of Quebracho blanco, hydrolyzed enzymatically and encapsulated in microcapsules, silkworm extract with phospholipids and water in gel, WO99/66881, active complex according to Example 1.

EXAMPLE 3

Cream I, SPF 15

Phase A

Water q.s. ad 100, Glycerine 3.0, Xanthan Gum 0.4, Caffeine 0.5.

Phase B

Tribehenin PEG20 Esters 1.0, Stearic Acid 1.5, PEG100 Stearate Glyceryl Stearate 3.0, Dicaprylyl Carbonate 6.5, Cyclohexa-siloxane 3.0, Butyl Methoxydibenzoylmethane 3.0, Bis-Ethylhexyloxyphenol/Methoxyphenyl Triazine 0.5, 4-Methyl Benzylidene Camphor 4.0, Tinosorb M® 3.0, Ethylhexyl Methoxycinnamate 7.5, Ethylhexyl Salicylate 5.0.

Phase C

RPF Complex* 0.15, UV-Pearls® 0.1, Colhibin® 0.5, Preservative 1.0, Photosomes® 0.6, Ultrasomes® 0.1, Soy Protein 0.5, Phototan® 0.5, Perfume 0.8.

Processing was done as in Example 1.

* Extract from the bark of Quebracho blanco, hydrolyzed enzymatically and encapsulated in microcapsules, silkworm extract with phospholipids and water in gel, WO99/66881, active complex according to Example 1.

EXAMPLE 4

Cream II, SPF 15

Instead of Butyl Methoxydibenzoylmethane and Bis-Ethylhexyloxyphenol/Methoxyphenyl Triazine, 3% ZnO and 5% $TiO_2$ were used and both were processed together with Phase A. The amount of Ethylhexyl Salicylate added was reduced to 1%. In all other respects, processing was done as in Example 1.

EXAMPLE 5

Cream I, SPF 30

Phase A

Water q.s. ad 100, Propylene Glycol 2.5, EDTA 0.1, Caffeine 0.5, $TiO_2$ 2.0.

Phase B

Isoamyl p-Methoxycinnamate 7.5, Butyl Methoxydibenzoylmethane 3.0, Parsol MCX® 4.0, Bis-Ethylhexyloxyphenol/Methoxyphenyl Triazine 2.0, 4-Methyl Benzylidene Camphor 2.0, Tinosorb M® 4.0, $SiO_2$ Powder 2.0, Dimethicone 2.0, Isopropyl Palmitate 3.0, Cetyl Ricinoleate 2.0.

Phase C

Ethanol 3.0, Colhibin® 0.5, RPF Complex* 0.1, Preservative 1.0, Photosomes® 0.6, Ultrasomes® 0.1, Soy Protein 0.5, Phototan® 0.5, Perfume 0.9.

Processing was done as in Example 1.

* Extract from the bark of Quebracho blanco, hydrolyzed enzymatically and encapsulated in microcapsules, silkworm extract with phospholipids and water in gel, WO99/66881, active complex according to Example 1.

EXAMPLE 6

Cream II, SPF 30

Instead of Butyl Methoxydibenzoylmethane, 1% ZnO and 7% $TiO_2$ were used and both were processed together with Phase A.

EXAMPLE 7

Pre-Sun Cream

Phase A

Water q.s. ad 100, Propylene Glycol 2.0, Glycerine 4.0, Carbomere 0.2, Caffeine 0.5.

Phase B

Cetearyl Alcohol 3.0, Beheneth-25 3.5, Dicaprylyl Carbonate 10.0, Dimethicone 5.0.

Phase C

Triethanolamine 0.2.

Phase D

Ethanol 5.0, Oligophycocorail Algae Extract 0.7, RPF Complex* 1.0, Preservative 1.0, Photosomes® 0.6, Ultrasomes® 0.1, Soy Protein 1.0, Phototan® 0.5, Perfume 0.8.

Processing was done as in Example 1, except that Phase C was added at 60° C. once Phases A and B had been combined.

* Extract from the bark of Quebracho blanco, hydrolyzed enzymatically and encapsulated in microcapsules, silkworm extract with phospholipids and water in gel, WO99/66881, active complex according to Example 1.

EXAMPLE 8

Pre-Sun Lotion

Phase A

Water q.s. ad 100, Propylene Glycol 1.0, Glycerine 7.0, Carbomere 0.08, Caffeine 0.5.

Phase B

Cetearyl Alcohol 5.0, Beheneth-25 4.0, Dicaprylyl Carbonate 12.0, Dimethicone 6.0.

Phase C

Triethanolamine 0.08.

Phase D

Ethanol 6.0, Oligophycocorail 0.5, RPF Complex* 1.0, Preservative 1.0, Photosomes® 0.6, Ultrasomes® 0.1, Soy Protein 1.0, Phototan® 0.5, Perfume 0.8.

Processing was done as in Example 7.

* Extract from the bark of Quebracho blanco, hydrolyzed enzymatically and encapsulated in microcapsules, silkworm extract with phospholipids and water in gel, WO99/66881, active complex according to Example 1.

EXAMPLE 9

After-Sun Cream

Phase A

Water q.s. ad 100, Butylene Glycol 3.0, Glycerine 4.0, EDTA 0.1, Caffeine 0.5.

Phase B

Cetearyl Alcohol 3.0, Beheneth-25 3.5, Dicaprylyl Carbonate 8.5, Dimethicone 2.0, Shea Butter 7.0.

Phase C

Ethanol 3.0, RPF Complex* 0.1, Water Melon Extract 0.1, Preservative 1.0, Photosomes® 0.1, Ultrasomes® 0.6, Soy Protein 1.0, Phototan® 0.8, Rose Extract 1.0, Jasminum Off. Extract 1.0, Perfume Oil 0.5.

Processing was done as in Example 1.

* Extract from the bark of Quebracho blanco, hydrolyzed enzymatically and encapsulated in microcapsules, silkworm extract with phospholipids and water in gel, WO99/66881, active complex according to Example 1.

EXAMPLE 10

After-Sun Lotion

Phase A

Water q.s. ad 100, Butylene Glycol 2.0, Glycerine 2.0, EDTA 0.1, Caffeine 0.5.

Phase B

Cetearyl Alcohol 1.0, Beheneth-25 3.5, Dicaprylyl Carbonate 10.0, Dimethicone 3.0, Shea Butter 5.0.

Phase C

Ethanol 4.0, RPF Complex* 0.1, Water Melon Extract 0.5, Preservative 1.0, Photosomes® 0.1, Ultrasomes® 0.6, Soy Protein 1.0, Phototan® 0.8, Rose Extract 1.0, Jasminum Off. Extract 1.0, Perfume Oil 0.5.

Processing was done as in Example 1.

* Extract from the bark of Quebracho blanco, hydrolyzed enzymatically and encapsulated in microcapsules, silkworm extract with phospholipids and water in gel, WO99/66881, active complex according to Example 1.

EXAMPLE 11

The composition corresponded to that of Example 3, except that, in addition, 1% creatine was added.

EXAMPLE 12

Comparative Example

The moisture in the skin of 12 female test persons with dry mixed skin was measured using a corneometer. The measurements were taken with a CM 825 corneometer (Courage & Khazaka, Germany) at 23° C. and 52% relative air humidity. The different creams were applied to the facial skin (cheeks) 2 hours after the skin had been cleansed.

| Time | Cream A | Cream B | Cream C |
| --- | --- | --- | --- |
| $t_0$ | 120 | 98 | 119 |
| after 4 h | 79 | 74 | 98 |
| after 8 h | 54 | 49 | 88 |
| after 12 h | 46 | 41 | 81 |
| after 24 h | 45 | 39 | 72 |

Cream A: Composition according to Example 10, but without caffeine/complex amino acid salt (Phototan ®)
Cream B: Composition according to Example 10, but without watermelon extract
Cream C: Composition according to Example 10

The comparative test shows that a content of 1.0% water melon extract in Cream C together with caffeine/complex amino acid salt clearly improves the binding of moisture in the skin, compared to Cream A, which only contained the water melon extract. After 24 h, this effect has to be considered as long-lasting effect.

EXAMPLE 13

Consumer Test

A consumer test was carried out, involving 100 female test persons aged between 35 and 56 years. In test phase 1, the test persons were given 3 commercially available creams/lotions, specifically a pre-sun product, a sun product with SPF 15 and an after-sun product made by renowned manufacturers. Said products were applied once a day for 14 days. Then, there was a pause lasting for 4 weeks. In the subsequent test phase 2, the test persons were given creams/lotions according to Examples 3, 8 and 10 of the invention. All test persons judged that the inventive products were clearly better. In detail, there were the following positive opinions in respect of the inventive product combination (in %):

| | |
|---|---|
| Refreshes | 90 |
| Reduces reddening | 91 |
| Immediate relief | 85 |
| Pleasant skin feeling | 96 |
| Soft skin | 99 |
| Regenerated skin | 93 |
| Golden tan | 86 |
| Long-lasting tan | 81 |
| Brilliant tan | 85 |
| Pleasant texture | 97 |
| Reduces irritations | 90 |
| Reduces sunburn | 85 |
| Long-lasting relief | 94 |
| Beautiful skin | 87 |
| Firm skin | 79 |
| More supple skin | 96 |
| More intensive tan | 70 |
| Even tan | 89 |
| Pleasant skin tone | 74 |

EXAMPLE 14

DNA Repair/Damage, In Vitro

In vitro tests (with Comet Assay=Single Cell Electrophoresis Assay; J. of Chromatography B 722 (1999) 225-247) were carried out using normal human keratinocytes. At the SPF stages 8 and 30, there was a DNA repair effect of +52% for keratinocytes which had been treated and exposed to radiation, compared to those which had been exposed to radiation without such treatment. DNA damage was reduced by approx. −83% at the SPF stages 8, 15 and 30.

EXAMPLE 15

Dermis Repair/Fibre Protection, In Vitro

In vitro tests (ELISA Immunoassay) were carried out using normal human fibroblasts. At the SPF stages 8, 15 and 30, there was a dermis repair effect of +20% for treated fibroblasts, compared to non-treated fibroblasts.

The dermis fibre protection of non-treated fibroblasts which had been exposed to UV radiation was −38%, compared to that of fibroblasts which had been treated and exposed to UV radiation. The amount of metal proteinase matrix was measured.

EXAMPLE 16

Tan In Vitro

In vitro tests were carried out using normal human melanocytes. At the SPF stages 8, 15 and 30, the amount of melanin was found to be increased by +45% after exposure to UVB radiation for treated melanocytes, compared to non-treated ones.

EXAMPLE 17

Skin Protection/Wrinkle Formation

The inventive product according to Examples 5, 7 and 9 was used in a clinical test involving 20 female test persons of Caucasian skin type. The product according to Example 5 was applied once a day for four days prior to exposure to UV radiation, the product according to Example 9 was applied for 3 days after exposure to UV radiation. Then, the evaluation took place.

FIG. 1 shows the electron microscopic images of non-protected skin which was not exposed to radiation (A), as well as of non-protected skin which was exposed to UV radiation (B) and of protected skin which was exposed to UV radiation (C). In case of C, the wrinkle depth is clearly reduced and the skin's appearance is clearly better, compared to B.

EXAMPLE 18

UV Protection

Cell analyses in order to determine the influence of the protection provided by the filter combination at SPF 8, 15 and 30 had the following result:

| | SPF 8 | SPF 15 | SPF 30 |
|---|---|---|---|
| % UVA stopped | 74 | 85 | 89 |
| % UVB stopped | 87 | 93 | 97 |
| % UVA + UVB stopped | 88 | 91 | 94 |

The invention claimed is:
1. A method for treating the skin with a kit of sun products, characterized in that, prior to intensive exposure to UV radiation, a pre-sun product as the first part of the kit is applied to the skin one to several time(s) a day for between 2 and 7 days, which product comprises as essential ingredients
   a radical scavenger,
   caffeine and a complex with amino acid salts consisting of sorbitol, arginine-HCl, ornithine-HCl, tyrosine and $SiO_2$,
   an enzyme photolyase enclosed in liposomes and UV endonuclease, and
   an extract from *corallina officinalis* with propylene glycol, during intensive exposure to UV radiation, a sun product as the second part of the kit is applied to the skin, comprising UVA filters and UVB filters and containing at least 3% by weight of UVA filters, relative to the total weight of the sun product, wherein the ratio of UVA and UVB filters is 1:1.8-2.2;
   and after intensive exposure to UV radiation, an after-sun product as the third part of the kit is applied to the skin at least once or one to several time(s) for between 1 and 7 days, which product comprises the same ingredients as the pre-sun product, the content of the radical scavenger and the enzyme photolyase being 50-90% by weight lower, the content of the enzyme UV endonuclease being 50-90% by weight higher, compared to the pre-sun product and in both cases relative to the total weight of said products, and the extract being replaced with a cooling plant extract or a plant extract mixture selected from the group consisting of water melon extract, which makes up 0.1-0.2% by weight, and a mixture of water melon extract, rose flower extract and jasmine flower extract which makes up 1.5-2.5% by weight, each relative to the weight of the after-sun product, wherein the extracts of water melon, rose flower and jasmine flower are water/glycerine extracts.

2. The method according to claim 1, wherein the pre-sun product is applied two to three times a day for between 5 and 7 days.

3. The method according to claim 1, wherein the after-sun product is applied two to three times a day for between 3 and 6 days.

4. The method according to claim 1, wherein a sun product is applied which contains at least 3.5% by weight of organic UVA filters, of which 0.3 to 0.7% by weight is a photostable organic UVA filter and 2.8 to 3.2% by weight is not a photostable organic UVA filter, relative to the total weight of the sun product.

5. The method according to claim 4, wherein the sun product has a sun protection factor (SPF) between SPF 8 and SPF 30.

6. A kit consisting of a pre-sun product, a sun product and an after-sun product,
the pre-sun product as the first part of the kit comprising as essential ingredients
  a radical scavenger,
  caffeine and a complex with amino acid salts consisting of sorbitol, arginine-HCl, ornithine-HCl, tyrosine and $SiO_2$,
  an enzyme photolyase enclosed in liposomes and UV endonuclease, and an extract from *corallina officinalis* with propylene glycol,
the sun product as the second part of the kit comprising UVA filters and UVB filters and containing at least 3% by weight of UVA filters, relative to the total weight of the sun product, wherein the ratio of UVA and UVB filters is 1:1.8-2.2;
and the after-sun product as the third part of the kit comprising the same ingredients as the pre-sun product, the content of the radical scavenger and the enzyme photolyase being 50-90% by weight lower, the content of the enzyme UV endonuclease being 50-90% by weight higher, in both cases relative to the total weight of said products, and the extract being replaced with a cooling plant extract or plant extract mixture selected from the group consisting of water melon extract, which makes up 0.1-0.2% by weight, and a mixture of water melon extract, rose flower extract and jasmine flower extract which makes up 1.5-2.5% by weight, each relative to the weight of the after-sun product, wherein the extracts of water melon, rose flower and jasmine flower are water/glycerine extracts.

7. The kit according to claim 6, wherein said product is a set consisting of the pre-sun product, the sun product and the after-sun product whose weight ratio is 1:0.5-2:0.8-1.

8. The kit according to claim 6, wherein the pre-sun product and the after-sun product each contain as radical scavenger an active complex consisting of an extract from the bark of quebracho blanco which subsequently has been hydrolyzed enzymatically and is encapsulated in microcapsules, a silkworm extract containing the peptide cecropine, amino acids and vitamins, in combination with phospholipids and an ionic or non-ionic gel and water.

9. The kit according to claim 6, wherein the radical scavenger makes up 0.1-2% by weight, the caffeine and the complex with amino acid salts together make up 0.01-3.0% by weight, the caffeine content being max. 0.5%, photolyase and UV endonuclease together make up 0.1-1.5% by weight, the extract of *corallina officinalis* makes up 0.2-2.5% by weight, and plant extract makes up 0.1-2.5% by weight, all percentages being relative to the total weight of the sun product concerned.

10. The kit according to claim 6, wherein the sun product or the after-sun product or both products contain as an additional active agent 0.5-3.0% by weight of an active complex consisting of 1 to 9% by weight creatine or a creatine derivative, 0.1 to 40% by weight of water-soluble glycogen, 1 to 10% by weight of a phospholipid, 0.1 to 5% by weight of a cosmetically acceptable gel, water making up the remainder up to 100% by weight, the aforesaid percentages being relative to the total weight of the complex and the mixture of creatine, glycogen and phospholipid being distributed homogeneously in the aqueous gel.

11. The kit according to claim 6, wherein each constituent of the kit contains additional auxiliaries, carriers or further active agents.

12. The kit according to claim 6, wherein the pre-sun product has a radical protection factor of $60\text{-}2{,}000 \times 10^{14}$ radicals/mg.

13. The kit according to claim 6, wherein the content of the radical scavenger in the sun product and in the after-sun product is 80-90% below the content in the pre-sun product.

14. The kit according to claim 6, wherein the content of the enzyme photolyase in the after-sun product is 75-90% below the content in the pre-sun product.

15. A kit consisting of a pre-sun product, a sun product and an after-sun product,
the pre-sun product as the first part of the kit comprising as essential ingredients
  a radical scavenger,
  caffeine and a complex with amino acid salts consisting of sorbitol, arginine-HCl, ornithine-HCl, tyrosine and $SiO_2$,
  an enzyme photolyase enclosed in liposomes and UV endonuclease, and an extract from *corallina officinalis* with propylene glycol,
the sun product as the second part of the kit comprising UVA filters and UVB filters containing at least 3% by weight of UVA filters, relative to the total weight of the sun product, wherein the ratio of UVA and UVB filters is 1:1.8-2.2, and wherein the UVA filters are up to 3% by weight butyl methoxydibenzoylmethane and up to 0.5% by weight bis-ethylhexyloxyphenol/methoxyphenyl triazine,
and the after-sun product as the third part of the kit comprising the same ingredients as the pre-sun product, the content of the radical scavenger and the enzyme photolyase being 50-90% by weight lower, the content of the enzyme UV endonuclease being 50-90% by weight higher, in both cases relative to the total weight of said products, and the extract being replaced with a cooling plant extract or plant extract mixture, selected from the group consisting of water melon extract, which makes up 0.1-0.2% by weight, and a mixture of water melon extract, rose flower extract and jasmine flower extract which makes up 1.5-2.5% by weight, each relative to the weight of the after-sun product, wherein the extracts of water melon, rose flower and jasmine flower are water/glycerine extracts.

* * * * *